United States Patent [19]
Garnier et al.

[11] Patent Number: 6,050,971
[45] Date of Patent: Apr. 18, 2000

[54] SUCTION CONTROL DEVICE FOR AN APPARATUS USED IN MICROSURGERY IN PARTICULAR IN OPHTHALMIC SURGERY

[76] Inventors: Bernard Garnier, 25 rue Mauvoisins, 44200 Nantes; Bernard Colin, 48 rue Jean Bouin, 44100 Nantes, both of France

[21] Appl. No.: 09/010,179

[22] Filed: Jan. 21, 1998

[51] Int. Cl.[7] .................................................. A61M 3/00
[52] U.S. Cl. .............................................. 604/43; 604/35
[58] Field of Search ................................. 604/22, 35, 40, 604/73, 119, 121, 43, 44

[56] References Cited

U.S. PATENT DOCUMENTS

| | | | |
|---|---|---|---|
| 4,516,398 | 5/1985 | Wuchinich | 604/22 |
| 4,573,979 | 3/1986 | Blake | 604/35 X |
| 4,705,500 | 11/1987 | Reimels et al. | 604/35 |
| 5,163,433 | 11/1992 | Kagawa et al. | 604/22 X |
| 5,586,977 | 12/1996 | Dorsey, III | 604/264 |

FOREIGN PATENT DOCUMENTS

| | | |
|---|---|---|
| 342448 | 11/1989 | European Pat. Off. . |
| 391511 | 10/1990 | European Pat. Off. . |
| 558846 | 9/1993 | European Pat. Off. . |
| 481638 | 1/1970 | Switzerland . |
| 8607249 | 12/1986 | WIPO . |

Primary Examiner—Wynn Wood Coggins
Assistant Examiner—A. T. Nguyen
Attorney, Agent, or Firm—Sughrue, Mion, Zinn, Macpeak & Seas, PLLC

[57] ABSTRACT

Suction control device intended to be fitted on an apparatus used in surgery, in particular in ophthalmic microsurgery, said apparatus comprising a handpiece (1) which may or may not be fitted with an ultrasound transducer for fragmenting a body which is to be extracted from the eye, and equipped with an orifice (17) for suctioning debris and connected to a system for pump-activated suctioning of liquid containing debris, characterized in that it includes means (18, 20) which, in the event of at least partial obstruction of the suction orifice (17) of the handpiece (1), are used for maintaining a continuous circulation of liquid between the active end of the handpiece and the pump-activated suctioning system of the apparatus.

9 Claims, 2 Drawing Sheets

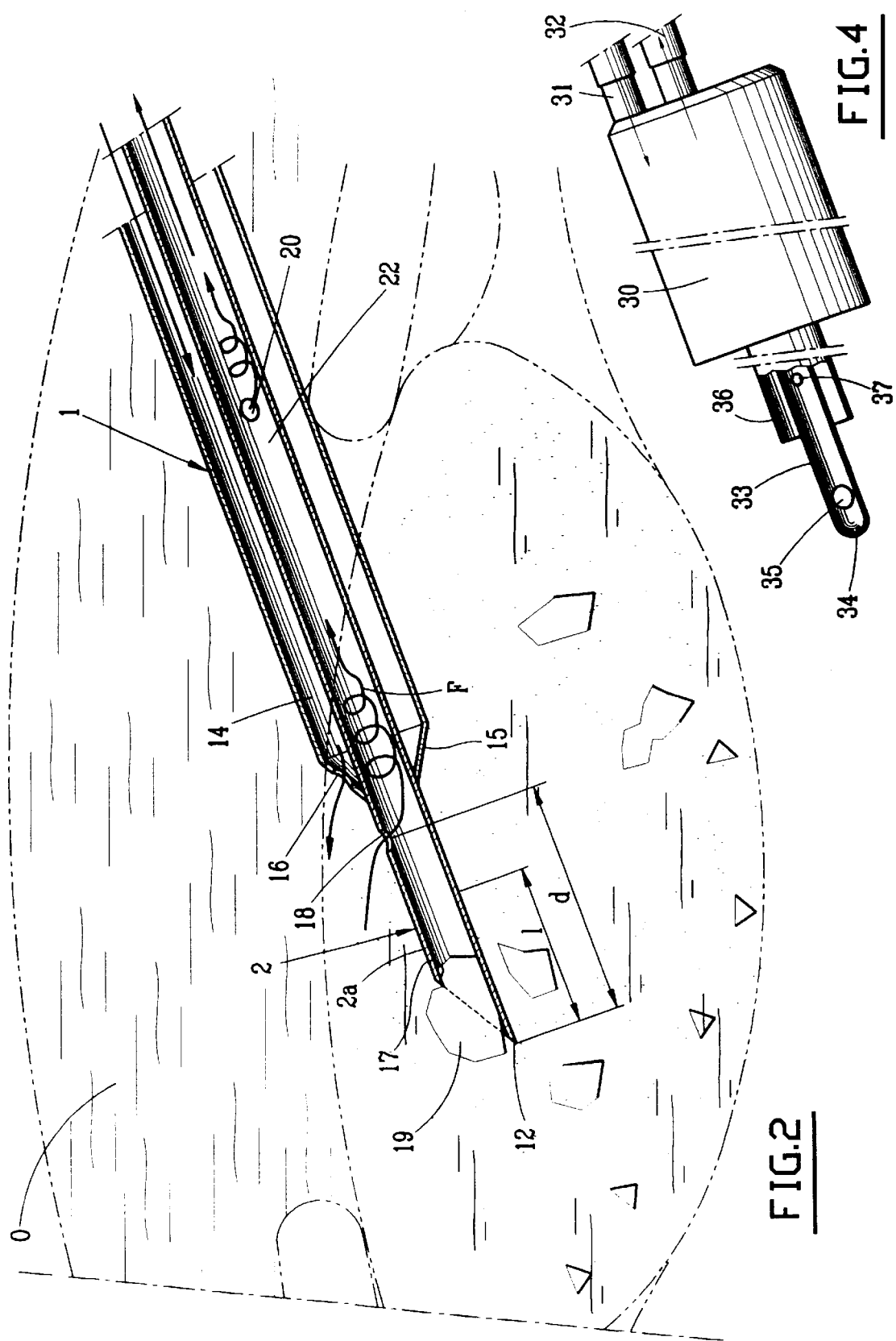

SUCTION CONTROL DEVICE FOR AN APPARATUS USED IN MICROSURGERY IN PARTICULAR IN OPHTHALMIC SURGERY

BACKGROUND OF THE INVENTION

The present invention relates to a suction control device designed to be fitted on the end of the handpiece of a lens extraction apparatus employed in ophthalmic surgery.

The general field of application of the invention is those cases where, during a surgical intervention, debris or liquids, in general organic, are to be suctioned from a cavity filled with fluid, for example the anterior chamber of the eye, and with greater safety, by means of strictly limiting all the effects and consequences of uncontrollable or poorly controlled suction.

All the lens extraction apparatuses currently available on the market are fitted with a suction pump connected via flexible lines to a handpiece which may be provided with an ultrasound transducer, said handpiece being maneuvered by the surgeon during the operation. The common feature of all these apparatuses is that the active end of the handpiece intended to penetrate the anterior chamber of the eye, so that ultrasound vibration triggers fragmentation of a body to be removed from the eye, includes only one suction orifice. It is very often found, during use, that when organic debris is being suctioned, obstruction of this single orifice, by a piece of debris, can have serious disadvantages.

The reason is that upon total obstruction or almost total obstruction of this single orifice, the suction pump, irrespective of the type used, continues to provide an underpressure, from its functional part to as far as the active end of the handpiece, the site of the obstruction. As the underpressure is maintained, a negative pressure thus prevails in the cavity formed by the line connecting the pump to the handpiece.

If the debris is finally suctioned, there is then a transitory uncontrolled phenomenon. The suction, on account of the abrupt removal of the obstruction, is amplified, firstly by the potential negative pressure of the column of liquid, present between the end of the handpiece and the pump, secondly, by the return of the walls of the line to the initial position, which walls, being slightly elastic, have caused a reduction in the volume of the column of liquid, and this because they are subjected to the action of the atmospheric pressure during the obstruction and to the underpressure caused by the pump.

Thus, when the active end of the handpiece is placed during the intervention in proximity to a thin organic membrane, such as the posterior capsule of the crystalline lens or the hyaloid membrane, this membrane is irrevocably and violently suctioned, the immediate consequence being its perforation by cutting against the active end of the handpiece. If an organ such as the iris is involved, this is also suctioned, with traumatic consequences. The size of the volume which has been violently suctioned in an unpredicted manner may empty the cavity of the anterior chamber of the eye, which, given the small volume of this cavity, can have serious consequences.

Various means such as calibrated or servo-controlled flaps or valves, electromechanical or electronic control devices connected to pressure sensors or flowrate sensors with a view to controlling the suction pump, prove to be ineffective in solving the existing problems. This is due, firstly, to the speed and suddenness of the transitory phenomena, secondly, to the inertia of the pump, thirdly, to the inertia of the column of liquid, fourthly, to the low values of the liquid volumes present, and, fifthly, to the very short distances, which are surgically necessary, separating the elements present.

It must also be noted that the value of the volume of the cavity of the anterior chamber of the eye is very much lower than the value of the volume existing between the active end of the handpiece and the suction pump. In the configuration presently employed in ophthalmic surgery, the active end of the handpiece is surrounded, over the greater part of its length, by a cylindroconical sleeve which is arranged concentrically, and provided with radial side orifices in its conical end part in proximity to the active end of the handpiece. Thus, there is an annular space between these two pieces since the internal diameter of the sleeve is greater than the external diameter of the active end of the handpiece, and this annular space is employed for infusion of a liquid whose dual role is to cool the active end driven by ultrasound oscillations, and also to replace the volume of suctioned liquid in order to keep the whole anterior chamber of the eye in its normal configuration, while maintaining its internal volume.

During the infusion of this liquid, which can be performed by gravity or by pumping, the inertia of the column of liquid, present between the infusion reservoir or pump and the radial outlets at the conical end of the sleeve, does not permit total and real-time replacement of the volume suctioned in the event of uncontrollable or inadequately controlled suctioning. The result of this is that despite this infusion, the problems set out above still remain. These phenomena, described here, are extreme in form, but there are also more subtle forms of these. There are in fact sub-occlusions, or occlusions of minimal duration, which occur during emulsification of organic fragments, and the transitory phenomena created by these sub-occlusions are responsible for numerous small pressure surges, which, although not having the serious nature of the extreme form of phenomena mentioned above, have harmful consequences for the eye which is being operated on; miosis, inflammation, etc.

SUMMARY OF THE INVENTION

The invention aims to remedy the disadvantages of the existing lens extraction apparatuses, in particular the apparatuses for phacoemulsification, by making available an apparatus of this type which, while being of a very simple construction and easy to use, generates practically no uncontrolled transitory phenomenon in the area of the suction orifice of the handpiece during suctioning of a piece of debris which is momentarily obstructing this orifice.

Another object of the invention is to accelerate the transit speed of debris and of the column of liquid moving during the suctioning.

It therefore relates to a suction control device intended to be fitted on an apparatus used in microsurgery, in particular in ophthalmic surgery, said apparatus comprising a handpiece, equipped with an orifice for suctioning liquid and debris contained in the latter, and connected to a system for pump-activated suctioning of liquid containing debris, characterized in that it additionally includes means which, in the event of at least partial obstruction of the suction orifice of the handpiece, are used for maintaining a continuous circulation of liquid between the active end of the handpiece and the pump-activated suctioning system of the apparatus.

According to a particular characteristic of the invention, said means for maintaining the circulation of liquid include at least one side orifice formed in the wall of the distal end of the handpiece.

According to another characteristic of the invention, the means for maintaining the circulation of the liquid are made up of a suction orifice formed at the distal end of the handpiece, provided with at least one fluting which permits a passage to remain for the liquid between the wall of said orifice and a piece of debris which is obstructing it.

The invention will be better understood from reading the following description which is given solely by way of example and where reference is made to the attached drawings, in which:

BRIEF DESCRIPTION OF THE DRAWINGS

FIG. 2 is a diagrammatic sectional view, on a larger scale, of a handpiece of the apparatus in FIG. 1, provided with the suction control device according to the invention;

FIG. 4 is a diagrammatic sectional view of an alternative handpiece intended for suction operations without prior fragmentation of the body which is to be removed.

DESCRIPTION OF PREFERRED EMBODIMENTS

Figures 1, 3:
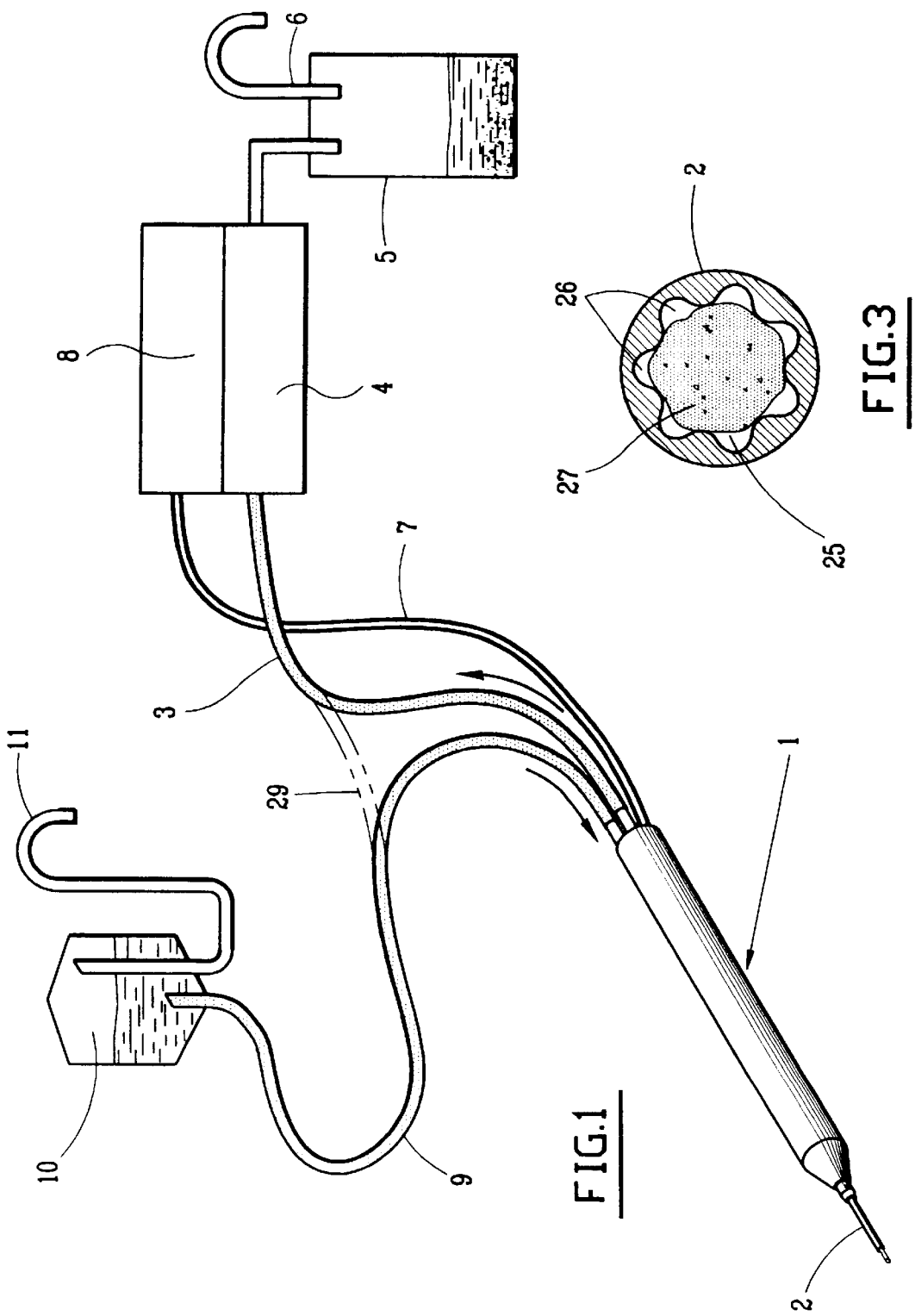
FIG. 1 is a diagrammatic view of an apparatus for phacoemulsification.
FIG. 3 is a transverse sectional view of another embodiment of the suction control device according to the invention.

FIG. 1 shows, in diagrammatic form, a phacoemulsification apparatus comprising a handpiece 1 equipped with an ultrasound transducer (not shown) for causing vibration of a hollow needle 2 connected via a flexible line 3 to a pump-activated suctioning system 4 which is in turn connected to a container 5 for recovering the debris and the liquid suctioned, and provided with a tube 6 to the outside air.

The transducer contained in the handpiece 1 is connected, via electrical power leads 7, to an ultrasonic frequency current generator 8.

The handpiece additionally includes a conduit of annular cross section surrounding the continuation of the needle 2 inside the handpiece, and connected via a flexible line 9 to a reservoir 10 which infuses the liquid by gravity and is provided with a tube 11 to the outside air.

As can be seen clearly in the diagrammatic sectional view in FIG. 2, the hollow needle 2 includes a beveled end 12 whose angle varies as a function of the anticipated use, and in which an axial suction orifice opens out.

The needle 2 continues inside the handpiece 1 and is connected, at its opposite end, to the flexible line 3, and with the aid thereof, to the pumping system 4 (FIG. 1). Formed between the hollow needle 2 and the wall of the handpiece 1 is the aforementioned annular channel or conduit 14, which is connected, as indicated in FIG. 1, via the flexible line 9 to the reservoir 10 for infusion by gravity, and including, at its end near the free end of the needle 2, a truncated portion 15 provided with radial orifices 16.

The annular conduit 14 has a cross section equal to or greater than that of the suction orifice 17 of the needle 2.

The liquid infused from the infusion reservoir 10 by gravity circulates in the annular conduit 14 and then flows through the radial orifices 16 of the truncated end 15 of the sleeve-shaped wall of the handpiece 1.

Formed in the free end portion of the needle 2 there is a radial side orifice 18 which, in the event of at least partial obstruction of the suction orifice 17 of the needle 2, forms a means of maintaining a continuous circulation of liquid between the active end of the needle 2, that is to say of the handpiece, and the suction pump of the pumping system 4.

In the present embodiment, the orifice 18 is placed at a distance d from the tip of the needle 2 and, consequently, from the end of the suction orifice 17 thereof, greater than the maximum length 1 of a piece of debris, such as the debris 19, capable of obstructing said orifice. The cross section of the radial orifice 18 is smaller than that of the suction orifice 17 of the needle 2.

In the embodiment in FIG. 2, the needle 2 includes, in its portion inside the handpiece, a second radial orifice 20 which can be of the same cross section as the orifice 18, bringing the inside of the needle into communication with the annular channel 14, and of which the axis is arranged orthogonal to that of the orifice 18.

Of course, it is also possible to provide a plurality of other orifices such as orifice 18 arranged radially on the circumference of the needle 2.

When the needle is introduced into the anterior cavity of the eye 0, represented in dot-and-dash lines in FIG. 2, and after the needle 2 of the handpiece has been set in vibration by the transducer (not shown) by the action of the ultrasonic wave generator 8 and has caused rupturing and consequently the fragmentation of the body which is to be extracted from the eye, the pumping system 4 causes the suctioning of the liquid containing the debris of the body to be extracted, mixed with the infusion liquid issuing through the orifices 16 of the handpiece 1 and originating from the reservoir 10 for gravity infusion.

When, as is represented in FIG. 2, a piece of debris such as the debris 19 totally or partially obstructs the suction orifice 17 of the needle 2, the possible flowrate for this orifice becomes zero or decreases in large proportions.

It is at this stage that the pseudo diversion, represented by the side orifice or orifices 18 formed in the end of the needle 2 engaged in the cavity of the eye ensures, by maintaining the suctioning of the pumping system 4, the circulation of a reduced volume of liquid, the consequence of which is to allow the column of liquid 22 situated between the tip of the needle and the pumping system to be kept constantly moving, in which case even a small flowrate is then established from the piece of debris 19, obstructing the end of the suction orifice 17, as far as the pump of the pumping system 4 (FIG. 1).

By virtue of the particular arrangement of the orifice or orifices 18 with an axis perpendicular to the wall of the needle, the flowrate of the liquid surrounding this zone of the needle sees its speed increased in immediate proximity to the orifice or orifices 18, and this happens on each side of the wall of the active part 2a of the needle 2.

More particularly, inside this active part 2a, a turbulent hydrodynamic state establishes itself, as represented by the arrow F, which has a beneficial effect on the speed of transit of the column of liquid 22 by virtue of the turbulences which counter the slow state of laminar flow which normally establishes itself in proximity to the walls.

On account of the flowrate of liquid passing through the orifice or orifices 18, it will be understood that the very great majority of the various veins of liquid which make up the column of liquid 22 move at almost homogeneous speeds, and with much less parasitic friction along the inner walls of the active end 2a the needle 2, and thus the speed of suction is increased in appreciable proportions.

From the point of view of the transitory phenomena, it will thus be understood that as the column 22 is still kept moving, the suction tube 3 (FIG. 1) retains its initial internal volume because it is subjected to the atmospheric pressure on its outer walls and to a constant negative pressure, provoked by the pump of the pumping system 4 and limited by the cross section of the orifice or orifices 18, on its inner walls. The tube 3 is thus never subject to abrupt variations in its internal volume, so that there is never any effect of amplification of the value of the suctioned volume, as would be found in the known apparatuses of the prior art.

Because of the particular arrangement of the radial orifice or orifices 18, as well as their adapted cross section, there is no reduction in the suctioning power at the level of the orifice 17.

As is represented in the embodiment in FIG. 2, the orifice 20 formed in the side wall of that portion of the needle 2 situated inside the handpiece 1, and consequently at a greater distance from the end of the active part 2a of the needle 2 than the distance d which separates the tip of the needle from the orifice 18 formed in this active zone 2a, also establishes a state of turbulence, which further increases the speed of suctioning without penalizing the suctioning power, and provides, in a beneficial manner, still further enhanced control during the brief partial occlusions of the suction orifice 17 of the needle, and also of the orifice 18.

According to a variant of the invention represented in FIG. 3, the needle 2 includes, at its distal end, a suction orifice 25 which has flutings 26 which, in the event of obstruction of the orifice 25 by a piece of debris such as 27, ensure a pseudo diversion of the liquid suctioned by the pump, and thus maintain a continuous movement of the column of liquid between the tip of the needle 2, obstructed by the debris 27, and the pumping system 4 (FIG. 1).

This is because the inner surface of the suction orifice 25 is undulated by virtue of the presence of the flutings 26 in such a way as to permit a lateral passage of the liquid in the event of occlusion of this orifice by a piece of debris.

The lateral veins of liquid circulating via the flutings 26 create a flowrate of liquid and thereby ensure that the column 22 (FIG. 1) is kept moving, in such a way that control of the suction is thereby obtained.

In the preferred embodiment of the invention, and in order to keep the entire column of liquid 22 moving, the orifice or orifices 18 are made in the side wall of the active part of the needle 2 in almost immediate proximity to the site of the obstruction.

However, this orifice, or these orifices, can be made at any other location on the needle 2.

The control effect is nevertheless maximal when the entire column of liquid 22 is in movement.

According to another embodiment, and in order to avoid any tendency for the cross section of the column of liquid 22 to decrease, it is also possible to use a calibrated communication between the suction line 3 and infusion line 9. This communication, represented in dot-and-dash lines in FIG. 1, and designated by the reference number 29, can be made at any location on the suction line 3 between the point of obstruction of the suction orifice of the needle 2 and the pumping system 4 and, also, at any location on the infusion conduit 9.

In addition, to overcome the inertia of the column of liquid from the infusion, the communication is preferably established at the end of the infusion column in almost immediate proximity to the site of the obstruction.

Thus, the two columns of liquid are at all times moving in their entirety.

FIG. 4 shows, in cross section, a handpiece which is intended for the suction operations alone.

This handpiece is used when it is necessary to remove, from the eye, particles of very small dimensions and of rather gelatinous consistency.

It includes a body 30 connected at one end to an infusion conduit 31 and a suction conduit 32, connected respectively in turn to a reservoir for infusion by gravity and to a pumping system which are analogous to those in FIG. 1.

At its end, the body 30 carries a needle 33 which is finer than the needle 2 of the apparatus represented in FIGS. 1 and 2.

The needle 33 includes a solid, rounded end 34, and a suction orifice 35 is formed in the lateral surface of the needle in proximity to said solid end 34.

The needle 33 is surrounded by a sleeve 36, for example made of silicone, for delivery of the infusion liquid.

A lateral orifice 37 having a cross section smaller than that of the suction orifice 35 is formed in the needle 33 in a position near its proximal end, via which it is connected to the handpiece.

This lateral orifice 37, whose cross section is, for example, of the order of a third of that of the suction orifice 35, ensures continuous movement of the column of liquid between the needle 33 and the suctioning system (not shown) in the event of momentary obstruction of the suction orifice 35 by a piece of debris which is to be removed.

It will be evident from the above description that the suction control device according to the invention can be used with all the existing lens extraction apparatuses regardless of the suction pump system used.

The suction control device of the invention is used without any modification being made to the lens extraction apparatus, without any variation in its mode of application, and, in particular, without requiring any modification in the nature or order of the surgical maneuvers performed by the surgeon.

It is entirely possible to use the suction control device with simple suction apparatuses, that is to say apparatuses not equipped with a fragmenting ultrasound transducer.

It does not require any training in its use.

What is claimed is:

1. A suction control device intended to be fitted on an apparatus used in microsurgery, in particular in ophthalmic surgery, said apparatus comprising a handpiece (1) equipped with a hollow needle (2; 33) having a debris-suctioning orifice (17; 35) opening out at the distal end of the needle and connected to means (4) for pump-activated suctioning of liquid containing debris, and a channel (14) for infusion of liquid for filling a surgical cavity (O) and for cooling, said device further comprising at least one additional orifice means (18; 20; 26; 37) for maintaining a continuous circulation of liquid between the surgical cavity (O) and the pump-activated suctioning means (4) in the event of at least partial obstruction of the suctioning orifice (17; 35) of the needle, said orifice means for maintaining the circulation being formed in that portion of the distal end of the needle (2) beyond and in front of the channel for infusing the liquid into the surgical cavity (O).

2. The suction control device according to claim 1, wherein said orifice means for maintaining the circulation of liquid is an orifice (18; 37) formed in a side wall of the distal end of the needle (2; 33) and has a cross section smaller than that of said suctioning orifice (17; 35).

3. The suction control device according to claim 2, wherein the handpiece (1) contains an ultrasound transducer for fragmenting a body to be extracted from an eye, and the suctioning orifice (17) of the needle is an axial orifice formed in the end thereof; and wherein said at least one orifice means (18) for maintaining the circulation of liquid is formed at a distance (d), from the tip of the needle, greater than the maximum length (1) for a piece of debris capable of obstructing the suctioning orifice (17) of the needle (2).

4. The suction control device according to claim 1, wherein the hollow needle (33) has a solid, rounded active distal end (34), the suctioning orifice (35) being formed in proximity to said rounded, solid end, and wherein said at least one orifice means (37) for maintaining the circulation of liquid has a cross section, smaller than that of the suctioning orifice (35), and a radial lateral arrangement in a wall of the needle (33) at a location near its proximal end via which it is fixed to the handpiece (30).

5. The suction control device according to claim 3, wherein the channel 14 is annular, surrounding the needle (2), and is provided at its end with orifices (16) for the infusion of the liquid for filling the surgical cavity (O) and for cooling, wherein said device further comprises at least one supplementary orifice means (20) for bringing the inside of the hollow needle (2) into communication with the annular infusion channel (14).

6. The suction control device according to claim 5, wherein said orifice means (18) for maintaining circulation is formed in an active part (2*a*) of the needle (2), and wherein said device further comprises radial orifice means (20) for bringing the inside of the hollow needle into communication with the annular infusion channel (14), the axis of the radial orifice means (20) for bringing the inside of the hollow needle (2) into communication with the annular channel (14) being orthogonal to the axis of the orifice means (18) for maintaining circulation.

7. The suction control device according to claim 1, wherein the suctioning orifice (25) is formed at the distal end of the handpiece and is provided with at least one fluting (26) permitting a passage to remain for the liquid between a wall of said suctioning orifice and a piece of debris which is obstructing said suctioning orifice, said fluting forming said suctioning orifice for maintaining circulation.

8. The suction control device according to claim 1, further comprising a first conduit (29) linking a second conduit (3), which connects the needle (2) to the pump-activated suctioning system (4), to a third conduit (9) which connects the channel (14), for infusion of liquid for filling the surgical cavity (O) and for cooling, to an infusion reservoir (10).

9. An apparatus used in microsurgery, in particular in ophthalmic surgery, comprising the suction control device according to claim 1.

\* \* \* \* \*